United States Patent [19]

Chavarria et al.

[11] Patent Number: 4,866,750
[45] Date of Patent: Sep. 12, 1989

[54] IMAGE RECEPTOR HOLDER AND BITE BLOCK DEVICE

[75] Inventors: Lazaro Chavarria, Missouri City; Tommie J. Morgan, Houston, both of Tex.

[73] Assignee: Board of Regents, The University of Texas System, Houston, Tex.

[21] Appl. No.: 31,398

[22] Filed: Mar. 27, 1987

[51] Int. Cl.[4] .............................................. G03B 42/02
[52] U.S. Cl. ..................................... 378/168; 378/170
[58] Field of Search ............... 378/167, 168, 169, 170, 378/205, 189, 191, 190, 168, 169, 170

[56] References Cited

U.S. PATENT DOCUMENTS

| | | | |
|---|---|---|---|
| 1,012,561 | 12/1911 | Ketcham | 378/168 |
| 1,404,171 | 1/1922 | Waite | 378/170 |
| 1,495,958 | 5/1924 | Machol | 378/168 |
| 1,608,269 | 11/1926 | Freund . | |
| 1,657,230 | 1/1928 | Simonton | 378/170 |
| 1,917,851 | 7/1933 | Paule | 378/191 |
| 1,963,702 | 6/1934 | Jackson . | |
| 2,127,502 | 8/1938 | De Weal | 378/168 |
| 2,245,395 | 6/1941 | Goldberg | 378/170 |
| 3,003,062 | 10/1961 | Updegrave . | |
| 3,134,900 | 5/1964 | Bersusan et al. | 378/190 |
| 3,473,026 | 10/1969 | Updegrave . | |
| 3,864,576 | 2/1975 | Stevenson . | |
| 3,930,164 | 12/1975 | Alexander | 378/189 |
| 3,936,643 | 2/1976 | Toner . | |
| 4,144,460 | 3/1979 | Norman . | |
| 4,598,416 | 7/1986 | Donato . | |

FOREIGN PATENT DOCUMENTS 708933 4/1952 United Kingdom .

OTHER PUBLICATIONS

Handout from the Mar. 23, 1986, Houston District Society Annual meeting.

*Primary Examiner*—Craig E. Church
*Attorney, Agent, or Firm*—Arnold, White & Durkee

[57] ABSTRACT

An image receptor holder and bite block device for positioning x-ray film in the mouth for radiography. The device permits the horizontal and vertical movement of the image receptor, which may be film or non-film, with respect to the x-ray source. The bite block is comprised of an upper and lower member which can rotate planarly with respect to each other. Multiple apertures along a vertical face of the bite block permits the vertical positioning of the bite block with respect to the x-ray source. The image receptor holder may also be rotatably connected to the bite block to permit vertical and horizontal movement of the image receptor holder with respect to the bite block. Articulation of the x-ray image receptor is made by pivoting various members of the device. Therefore, the device may be adjusted to accommodate the contours of a particular patient's mouth. The area of radiation can be minimized because the relative movement of the image receptor to the x-ray source is greatly reduced. Consequently the radiation exposure of the patient is reduced.

24 Claims, 4 Drawing Sheets

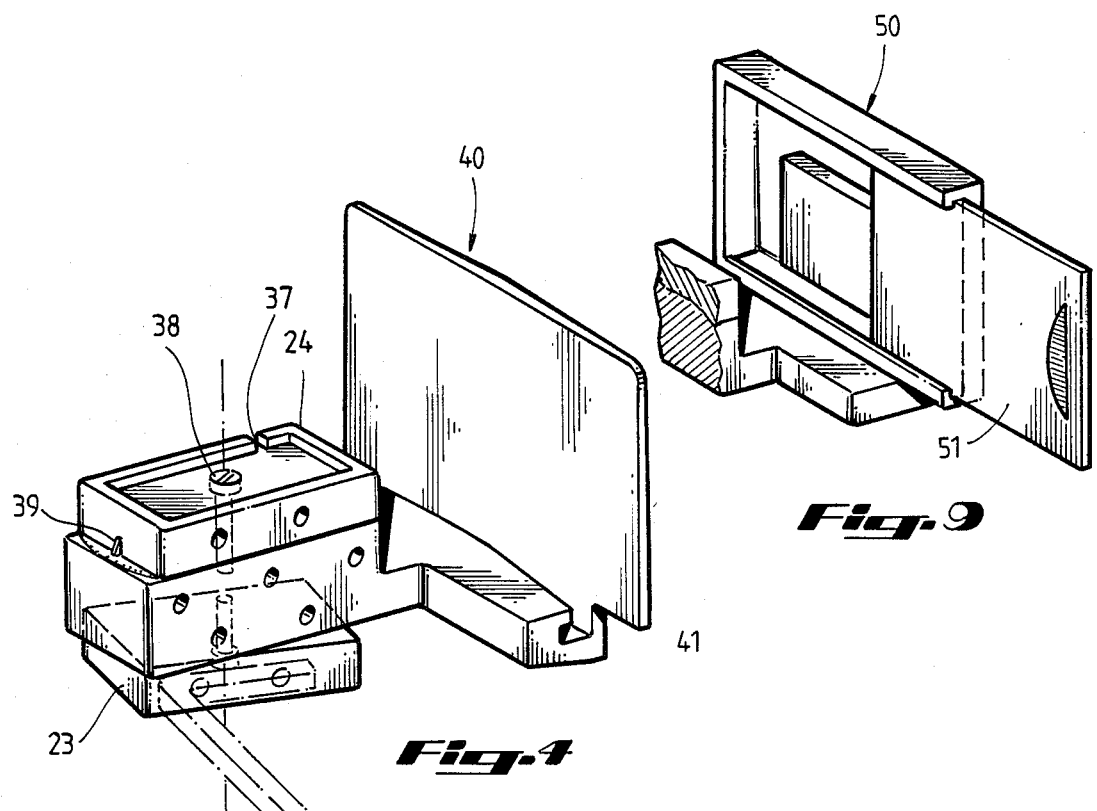
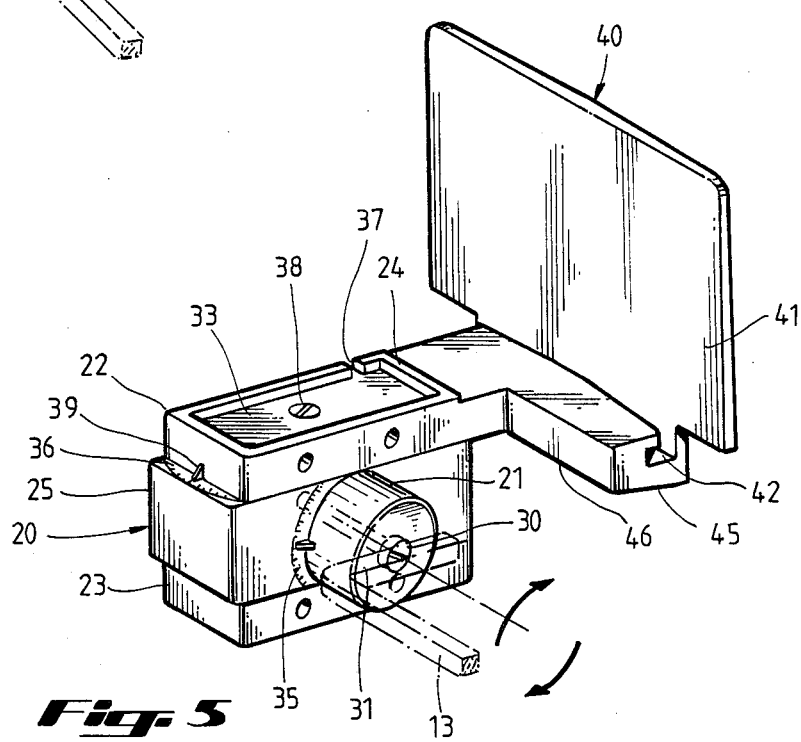

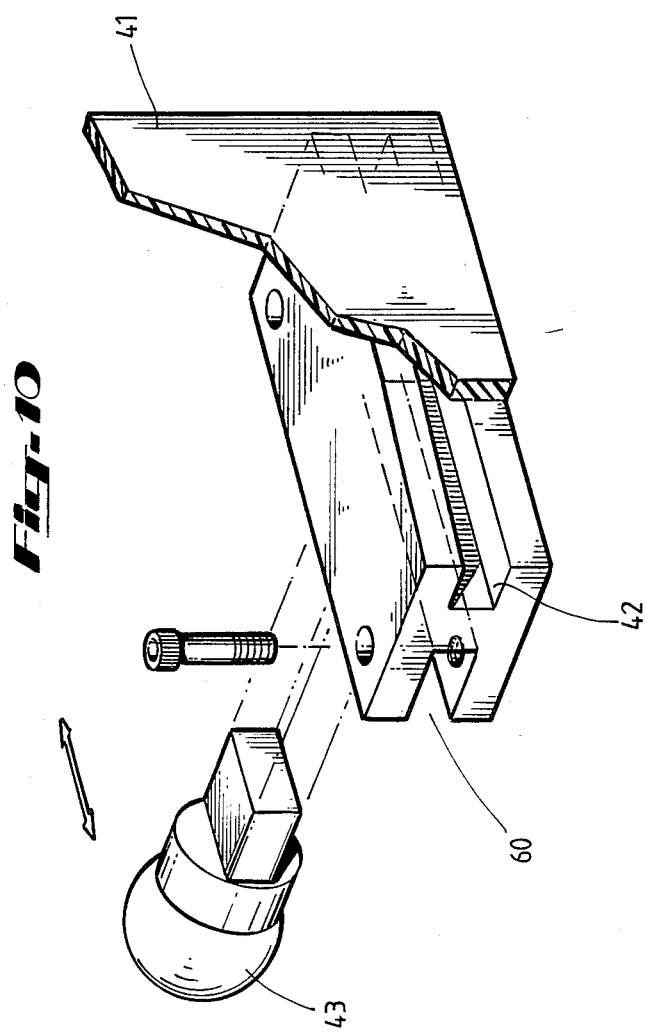

IMAGE RECEPTOR HOLDER AND BITE BLOCK DEVICE

BACKGROUND OF THE INVENTION

The present invention relates generally to a multigeometry image receptor holder and bite block device for use in radiographing teeth involved in dental procedures, such as endodontic, periodontic or oral surgery treatment. More particularly, the present device relates to a bite block and image receptor holder assembly which is individually rotatable about one or more axes so as to achieve a precise exposure angle for intraoral radiography, thus substantially reducing the irradiated cross-sectional area.

Endodontic treatment generally requires a battery of radiographic exposures to evaluate the pathologic state of the pulp of a damaged or diseased tooth. It is often necessary to create controlled radiographic image distortion to gain a clearer view of any overlapping roots, canals, etc., which may exist in and around the tooth. A practitioner can more accurately gauge the depth and position at which any such structure or object appears in or around the tooth by taking multiple radiographic images of the tooth from varying positions and applying the buccal object rule. The buccal object rule predicts the distortion caused by changing the angle with which the beam strikes the film.

Use of controlled image distortion requires that views be reproducible so that a particular image can be compared to a similar image taken at a later time. The radiographic view must remain constant with each exposure to insure that the variations observed in later radiographs are not caused by changing the angle of exposure. If the same view, or angle of exposure, is not maintained in each radiograph, then the changes observed may be caused by the positioning of the beam, film, or object.

The object to be observed may be a suspected tumor, carious lesion, or other hard structures of either animals or humans. In periodontics, it may be an infrabony pocket. In endodontics the observed object may be a periapical pathologic radiolucency.

In endodontic treatment, an instrument (usually a file) is placed within the pulp of the tooth. Since the file normally protrudes beyond the occlusal surface of the tooth, it is impossible to have the patient bite down on the bite block of a conventional image receptor holder to radiograph the tooth and file. Thus, any bite block and image receptor holder setup which is used in endodontic treatment must accommodate this problem by providing an offset between the bite block and the image receptor holder.

Several problems exist in utilizing conventional radiographic techniques in analyzing a tooth during endodontic treatment. One problem is the repeated exposure of the patient to overly broad areas of irradiation. Study has long shown that repeated x-ray exposure greatly increases the incidence of genetic or somatic abnormalities and promotes the development of malignant disease. While there exists considerable controversy on this subject, most authority concurs in the opinion that the incidence of abnormality or carcinoma increases in direct proportion to the Roentgen exposure/rad dose. Therefore, the greater the number of exposures, the greater the risk.

The risk of excessive radiation is increased during endodontic procedure because of the need to take multiple radiographs of the diseased tooth. In conventional oral diagnosis, one to two x-ray exposures are normally sufficient to fully analyze a tooth or adjacent group of teeth for disease, alignment, structure, etc. However, in endodontic treatment, the use of controlled image distortion often necessitates the placement of the radiographic film about the outer periphery of the x-ray exposure area, thus resulting in a number of inconclusive or "bad exposures." To compensate for these "bad exposures", the x-ray exposure field is often larger than required for imaging in order to bring the film well within the irradiated area. The x-ray beam is directed through a position indicating device ("PID") attached to the x-ray machine. The PID is typically round, rather than coincident with the rectangular area of the film thus resulting in a larger area being irradiated. This increase in the size of the irradiated field thus exposes unnecessary tissue to the risk of x-ray exposure. Also, the number of exposure is often multiplied because of the need to take duplicate exposures.

Several attempts have been made to design a bite block and image receptor holder device which would alleviate many of the problems encountered in endodontic treatment. One such design is seen in U.S. Pat. No. 4,598,416. This patent relates to a bite block and image receptor holder device having an adjustable support arm which may be pivoted in either a horizontal or vertical plane relative to the x-ray source. Rigidly attached to this support arm is a bite block and image receptor holder assembly. The film holding arm is offset from the bite block so that the x-ray film can be held securely behind the tooth to be x-rayed, despite the presence of files or other instruments in or about the tooth.

Disadvantages of this design include the lack of flexibility in positioning the bite block assembly relative to the x-ray source. In this design, the multiple pivot point is positioned on a support arm some distance from the bite block and image receptor holder assembly. No provision is made for an adjustment within the mouth of the patient so as to more precisely accommodate files or other instruments remaining in the mouth during the radiographic exposure, or to otherwise accommodate dental incongruities peculiar to any given individual.

Lack of flexibility in this design also requires an unnecessarily large area of irradiation. In operation, the alignment ring of this device is slidably attached to the long cone of the x-ray machine. The support arm members are then adjusted relative to each other to achieve a desired degree of angulation in both a horizontal and vertical plane. However, since the film holder and bite block assembly rotates a relatively long distance from the film, the cross section of the x-ray field (beam) must be kept fairly large in order to irradiate the film positioned behind the subject tooth. Therefore a round PID, as discussed above, must be used. Such a broad irradiation profile, especially when conducted over a period of time, often results in unnecessary x-ray exposure.

SUMMARY OF THE INVENTION

The present invention overcomes many of the disadvantages of prior art systems by providing a bite block and image receptor holder assembly which facilitates the taking of radiographs from various positions. The invention also allows the cross-sectional area exposed to radiation, to be minimized.

A preferred embodiment of the image receptor holder and bite block assembly of the present invention is generally comprised of a bite block, a mounting shaft and an image receptor holder. The bite block has an upper member and a lower member both of which can rotate in planes parallel to one another. The mounting shaft is attached to the bite block and allows the image receptor holder and bite block assembly to rotate around the axis of the mounting shaft. The mounting bracket is connectable to a support arm which can hold the image receptor holder and bite block assembly during dental procedures. The image receptor holder is attached to either the upper or lower pivotal members of the bite block. Also, the holder can hold either film or non-film type image receptors.

One feature of the present invention is that it allows greater flexibility in the angular positioning of the x-ray cone in relation to the film holding arm. Since the angular articulation of the present device is achieved within the bite block assembly itself, the bite block may be "customized" to fit the contours of the oral surface with which it is to be used. The degrees of horizontal and vertical articulation of the device may be measured and read on a scale provided on the moveable members.

Another feature of the present invention is that the bite block assembly may move in both a horizontal and vertical plane simultaneously, thus allowing the x-ray beam to strike the film at an angle, rather than being limited to parallel plane alignment, thus offering improved utilization of the buccal object rule.

Yet another feature of the present invention is that it permits the use of a rectangular PID rather than a round PID. By using the instant invention, a controlled image distortion or reposition can be accomplished by very minor changes in the position of the image receptor. Therefore, a rectangular PID having a radiation area about the same size as that of the image receptor can be used. This feature is especially valuable because it minimizes the overall surface area of the patient exposed to radiography.

Examples of some of the important features of this invention have been summarized above rather broadly in order that the detailed description that follows may be better understood, and in order that the contribution to the art may be better appreciated. There are, of course, additional features of the invention that will become apparent in the detailed description of the preferred embodiment as well as alternative embodiments of the present invention.

BRIEF DESCRIPTION OF THE DRAWINGS

FIG. 4 is another detailed side view of the image receptor holder and bite block showing the rotation of the lower member.

FIG. 5 is a detailed side view showing the shaft for rotation of the device.

FIG. 9 is a detailed view of the image receptor holder for holding non-film image receptors.

FIG. 10 is a view showing the slidable attachment of the image receptor holder to the bite block.

DETAILED DESCRIPTION OF THE INVENTION

Figure 1:
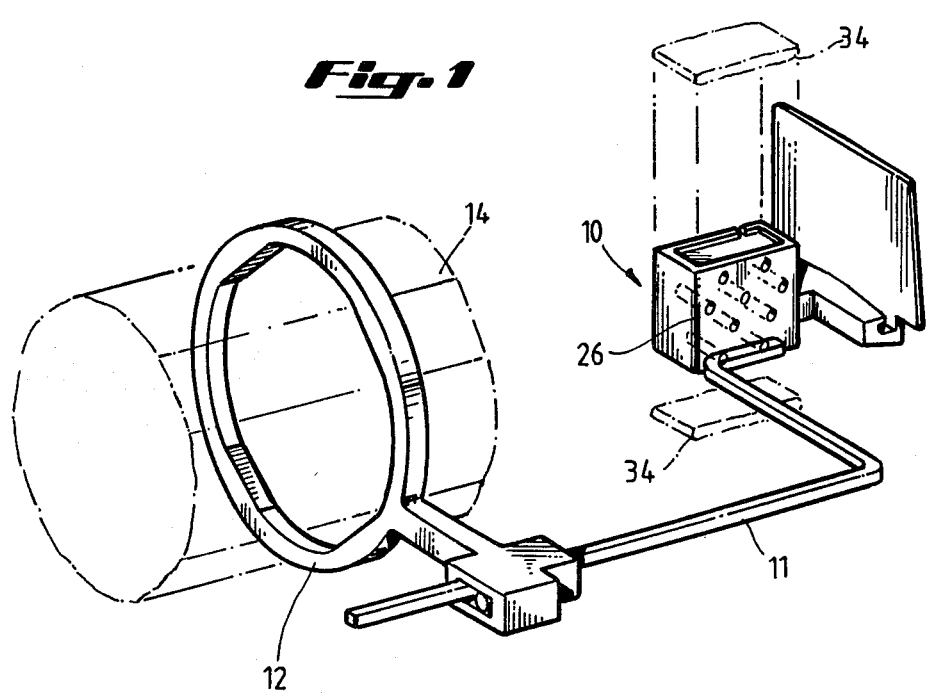
FIG. 1 is a perspective view of the image receptor holder and bite block device.

FIG. 1 is a perspective view of the image receptor holder and bite block device 10 attached to a support arm 11.

A preferred embodiment of the present device is shown in FIG. 5. The image receptor holder and bite block assembly 10 is rotatably secured to a mounting shaft 21 via a retaining pin 30 or other suitable pivot member. This retaining pin 30 is disposed parallel to the longitudinal axis of the bite block 20 so that the image receptor holder 40 and bite block 20 may rotate along an axis generally parallel to the upper and lower surfaces of the bite block. A plurality of mounting apertures 31 may be disposed along the face of the mounting shaft 21, opposite the bite block 20, so that it can be used with a conventional two-pronged attachment arm 13, such as seen in U.S. Pat. No. 3,473,026 and No. 4,598,416. The mounting shaft or hub 21 may assume a variety of shapes and sizes, but preferably is of a configuration which will not inhibit the free rotational movement of the upper 22 and lower 23 pivot members of the bite block 20. The mounting shaft 21 is snugly attached to the bite block 20, so that the bite block 20 does not freely rotate without some positive force being applied by the user to cause the rotation. Alternatively, the mounting shaft 21 may be constructed out of a material such as delrin, (acrylics or polymethyl-methacrylates) that does not freely allow unintended rotation of the bite block.

The image receptor holder and bite block assembly 10 may be easily adjusted to various horizontal and vertical positions relative both to the mouth of the patient and to the x-ray source. The bite block 20 is preferably constructed in three sections which are rotatably interconnected by a retaining pin 38 or other suitable pivot member which is disposed perpendicular to the longitudinal axis of the bite block, such that the upper 22 and lower 23 members of the bite block 20 may rotate planarly about a center section 25. This center section 25 in turn is rotatably connected to the mounting shaft 21 as previously mentioned. The upper 22 and lower 23 members of the bite block 20 may freely rotate even while the center section 25 is inclined relative to the mounting shaft 21. The upper 22 and lower 23 members may also rotate independently of each other if desired.

The degree of both vertical and horizontal angulation may be read and measured by calibrations 35 and 36 provided on the surface of either, or both, of the upper pivoting member 22 and the center member 25. A pointer 39 permits the positive positioning of the pivot member 22. Similar pointers may be located on the mounting shaft 21 and the lower pivoting member 23.

It is also envisioned in a preferred embodiment that the contact "bite" surfaces of the upper and lower members of the block be provided with a recessed tray or dish area 33 and 27, respectively, such that impression material, or the like, may be inserted for any given application. The impression material may be any rubber based or similar material known in the industry. A notch 37 is also provided on the pivot member 22 or 23 to facilitate the realignment of the impression material on the bite block for successive reproducible radiography.

The image receptor holder 40 is attached to the bite block's distal end 24 as viewed from the x-ray source and is offset from the center of the bite block 20 so as to allow the radiographic imaging of a tooth which is undergoing endodontic treatment.

In one preferred embodiment of the device, the image receptor holder 40 is designed to hold x-ray film and is comprised of an upright planar member 41 which distends generally in a vertical fashion from a support member 46 attached to the pivotal upper member 22. A slot or groove 42 may be provided at the lower end 45 of the planar member 41 to accommodate the x-ray film. In some embodiments, the planar surface 41 may be inclined relative to the support member 46 and in the direction of the x-ray source 14 so as to securely hold the film as it is placed in the groove or slot 42. In some embodiments, a metallic grid may be affixed to the exposed surface of this planar member so as to furnish a measurement standard for periodontic treatment.

In another embodiment of the invention as shown in FIG. 1, the bite block 10 is a rigid structure having multiple apertures 31 disposed along its vertical longitudinal face 26. The multiple apertures 31 permit vertical variations in the relationship between the support arm 11 and the image receptor holder 40.

Figure 2:
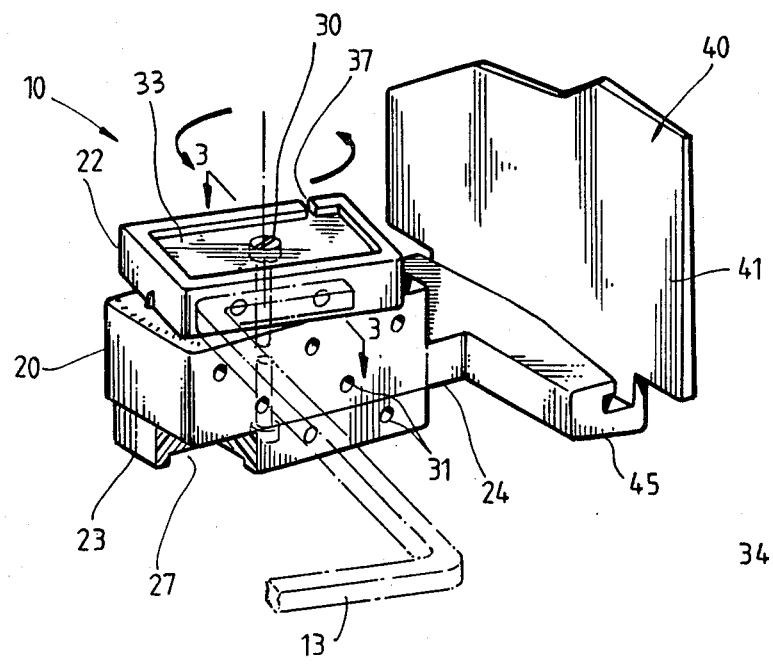
FIG. 2 is a detailed side view of the image receptor holder and bite block showing the rotation of the upper pivot member.
Figure 3:
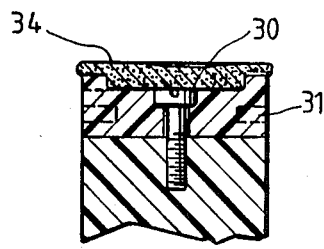
FIG. 3 is a cross-sectional view taken along line 3—3 in FIG. 2.
Figure 7:
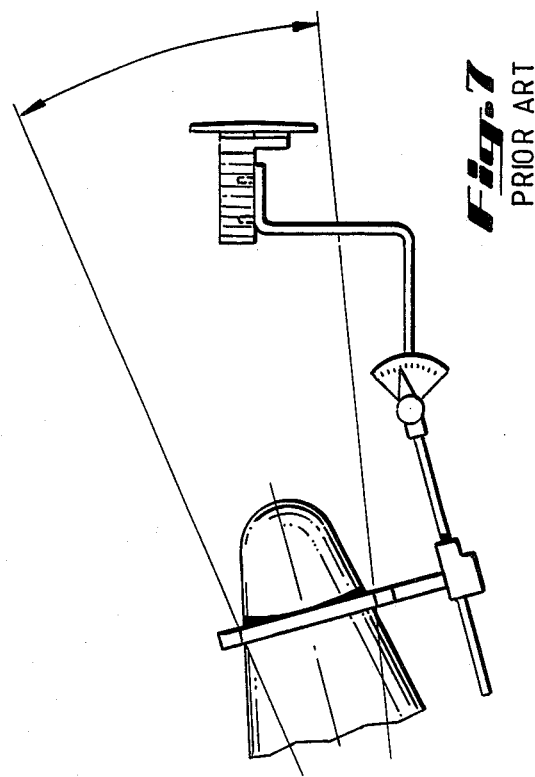
FIG. 7 depicts the wide area of radiation required by the prior art.

In yet another embodiment of the invention as shown in FIG. 2, the attachment arm 13 is attached to the upper pivot member 22. This arrangement permits the horizontal movement of the image receptor holder 40 in relation to the x-ray source 14. Multiple apertures 31 are also provided throughout the bite block 20 to permit the user to vary the vertical relationship between the image receptor holder 40 and the x-ray source 14.

The embodiment shown in FIG. 4 is basically the same as the embodiment shown in FIG. 2, except that the attachment arm 13 is connected to the lower pivot member 23.

Figure 6:
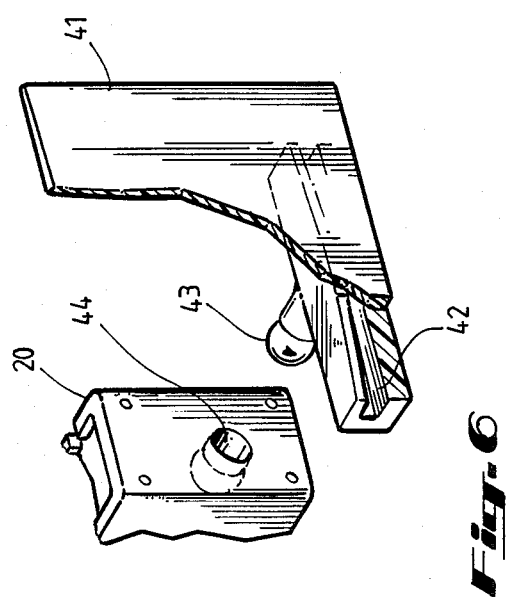
FIG. 6 is a detailed view of the ball and socket connection between the image receptor holder and the bite block.
Figure 8:
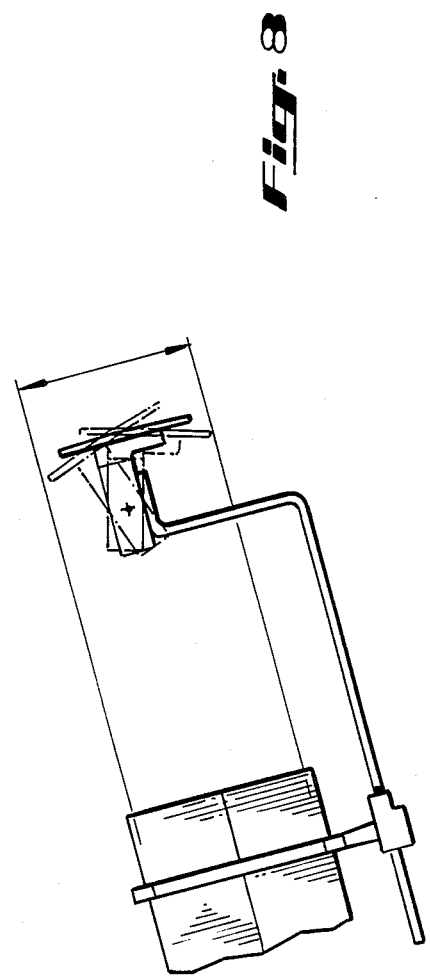
FIG. 8 depicts the narrower range of radiation resulting from the image receptor holder and bite block device.

In still another embodiment of the present device as shown in FIG. 6, the image receptor holder 40 may be rotatably attached to the bite block 20. The image receptor holder 40 is rotatably attached to the bite block 20 by means of a ball 43 and socket 44. The ball 43 and socket 44 joint can be made in the ordinary manner known in the art. Other suitable swivel means can also be used to allow rotation of the image receptor holder. This configuration permits even greater flexibility in diagnostic intraoral imaging since the image receptor holder 40 need not be aligned with the bite block 20. In another embodiment, the image receptor holder may also be slidably attached to the bite block 20 so that the image receptor holder 40 can be moved horizontally with respect to the bite block 20. Ordinary means known in the art, such as a slot 60, as shown in FIG. 10, may be used for allowing the lateral movement of the image receptor holder 40.

In another embodiment, the image receptor holder may be adapted to receive a non-film image receptor. Non-film image receptors respond to x-rays and absorb energy. For example, a non-film image receptor may be a solid state device. The distribution of the energy trapped by the receptor is proportional to the relative distribution of the incident x-ray on the non-film image receptor. This accumulated energy can be "read out" or measured with associated spatial information. This information is then digitized and displayed as a digital image.

FIG. 9 depicts an image receptor holder 40 which has been adapted to receive a non-film image receptor. The door 50 is shown as a slidably connected door, but it can also be hinged compression fit, or otherwise suitably attached to vertical tray 51. The non-film image receptor is placed within the tray 51 and door 50 is closed so that the receptor is not exposed to ambient light. The door 50 is made of any suitable plastic material which will permit the passage of x-rays. During radiography, the x-ray beam penetrates the door 50 and projects the image of the object onto the non-film image receptor.

Although the preferred embodiments of this invention have been described hereinabove in some detail, it should be appreciated that these embodiments are capable of variation and modification. The description of this invention is not intended to be limiting on this invention, but is merely illustrative of the preferred embodiments of this invention. Other image receptor holder and bite block devices which incorporate modifications or changes to the embodiments which have been described herein are equally included within this application.

What is claimed is:

1. An image receptor holder and bite block device for positioning radiographic image receptors within the mouth at a variety of angles with respect to a radiographic source, comprising:
a bite block having an upper member rotatably connected to a lower member such that the upper member can rotate laterally with respect to the lower member; and
an image receptor holder attached to said bite block's distal end as viewed from said radiographic source.

2. The image receptor holder and bite block device of claim 1 wherein said upper and lower members of said bite block each form a tray for receiving impression material.

3. The image receptor holder and bite block device of claim 1 wherein said upper and lower members have multiple apertures for receiving a support arm, such that said bite block is vertically positionable with respect to said support arm.

4. The image receptor holder and bite block device of claim 1 wherein the image receptor holder is rotatably attached to the bite block.

5. The image receptor holder and bite block device of claim 1 wherein said image receptor holder is attached to one of said rotatable upper and lower members.

6. The image receptor holder and bite block device of claim 1 wherein said image receptor holder comprises a tray and door for receiving a non-film image receptor, wherein said door can be slid over said tray to completely enclose said non-film image receptor.

7. The image receptor holder and bite block device of claim 1 further comprising means for measuring the position of the upper member relative to the lower member.

8. An image receptor holder and bite block device for positioning radiographic film within the mouth at a variety of angles with respect to a radiographic source, comprising:
a bite block having an upper member and a lower member which are rotatably connected so that said members may rotate planarly relative to each other;

a mounting shaft attached to a vertical face of the bite block; and an image receptor holder attached to said bite block's distal end as viewed from said radiographic source, said holder being offset from the center of said bite block.

9. The image receptor holder and bite block device of claim 8 wherein the mounting shaft is rotatably connected to said bite block by a retaining pin.

10. The image receptor holder and bite block device of claim 8 wherein said upper and lower members of said bite block each form a tray for receiving impression material.

11. The image receptor holder and bite block device of claim 8 wherein said upper and lower members have multiple apertures for receiving a support arm, such that said bite block is vertically positionable with respect to said support arm.

12. The image receptor holder and bite block device of claim 8 wherein the image receptor holder is rotatably attached to the bite block.

13. The image receptor holder and bite block device of claim 8 wherein said image receptor holder is attached to one of said rotatable upper and lower members.

14. The image receptor holder and bite block device of claim 9 further comprising means for measuring the vertical and horizontal position of the film holder.

15. The image receptor holder and bite block device of claim 8 further comprising means for measuring the position of the upper member relative to the lower member.

16. An image receptor holder and bite block device for positioning radiographic film within the mouth at a variety of angles with respect to a radiographic source, comprising:

a bite block having an upper member rotatably connected to a lower member such that the upper member can rotate laterally with respect to the lower member; and an image receptor holder attached to said bite block's distal end as viewed from said radiographic source, said holder being offset from the center of said bite block.

17. An image receptor holder and bite block device for positioning dental radiographic film within the mouth at a variety of angles with respect to a radiographic source, comprising:

a bite block having upper and lower members which are rotatably attached to a central member by a retaining pin, wherein said pin is disposed so that the upper and lower members may planarly rotate independently of each other;

a mounting shaft attached to a longitudinal vertical face of said bite block; and an image receptor holder attached to said bite block's distal end as viewed from said radiographic source, said holder being offset from the center of said bite block.

18. The image receptor holder and bite block device of claim 17 wherein said mounting shaft is rotatably connected to said bite block's central member.

19. The image receptor holder and bite block device of claim 17 wherein said image receptor holder is rotatably attached to said bite block.

20. The image receptor holder and bite block device of claim 17 wherein said upper and lower members of said bite block each form a tray for receiving impression material.

21. The image receptor holder and bite block device of claim 18 further comprising means for measuring the vertical and horizontal position of the film holder.

22. The image receptor holder and bite block device of claim 17 further comprising means for measuring the position of the upper member relative to the lower member.

23. An image receptor holder and bite block device for positioning radiographic film within the mouth of a patient, comprising:

a bite block having a plurality of apertures disposed across at least one vertical side of said block so that a support arm can be vertically positioned with respect to said bite block; and an image receptor holder rotatably attached to said bite block at its distal end as viewed from an x-ray source, said holder having a planar member substantially perpendicular to the longitudinal axis of said bite block and being offset from the center of said bite block.

24. The image receptor holder and bite block device of claim 23 wherein said image receptor holder is rotatably and slidably attached to said bite block.

* * * * *